United States Patent [19]

Karrer

[11] Patent Number: 4,971,981
[45] Date of Patent: Nov. 20, 1990

[54] SUBSTITUTED DIOXOLAN AND DIOXAN DERIVATIVES USEFUL AS PESTICIDES

[75] Inventor: Friedrich Karrer, Zofingen, Switzerland

[73] Assignee: Ciba-Geigy Corporation, Ardsley, N.Y.

[21] Appl. No.: 145,432

[22] Filed: Jan. 19, 1988

[30] Foreign Application Priority Data

Jan. 19, 1987 [CH] Switzerland ............................ 177/87

[51] Int. Cl.$^5$ ...................... A01N 43/28; A01N 43/32; C07D 317/22; C07D 319/12
[52] U.S. Cl. .................................... 514/336; 549/453; 549/451; 549/444; 549/443; 549/435; 549/378; 549/362; 549/347; 549/342; 546/284; 546/283; 546/270; 546/268; 514/467; 514/466; 514/464; 514/462; 514/452; 514/338
[58] Field of Search ................ 549/448, 453, 435, 60, 549/451, 444, 443, 342, 347, 378, 362; 546/270, 283, 284, 268; 514/467, 466, 464, 462, 452, 338, 336

[56] References Cited

U.S. PATENT DOCUMENTS

| | | |
|---|---|---|
| 4,007,280 | 2/1977 | Karrer . |
| 4,097,581 | 6/1978 | Farooq et al. .................. 549/453 |
| 4,100,296 | 7/1978 | Farooq et al. .................. 549/453 |
| 4,590,282 | 5/1986 | Henrick . |

OTHER PUBLICATIONS

Frear et al., J. Economic Entomology, vol. 40, pp. 736–741 (1947).

Primary Examiner—Nicky Chan
Attorney, Agent, or Firm—Kevin T. Mansfield; Edward McC. Roberts

[57] ABSTRACT

Novel substituted 1,3-dioxolan and 1,4-dioxan derivatives of formula I

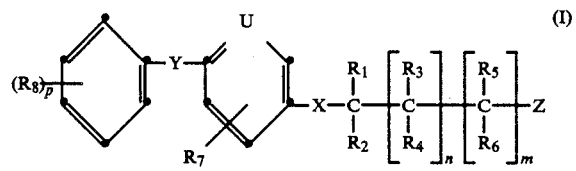

in which
$R_1$, $R_2$, $R_3$, $R_4$, $R_5$ and $R_6$ each independently of the others represents hydrogen or $C_1$–$C_4$-alkyl or, if n=1,
$R_2$ and $R_4$ together represent one of the radicals

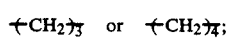

$R_7$ represents hydrogen, halogen, methyl, ethyl, $C_1$–$C_2$-alkyl substituted by 1 to 5 halogen atoms, methoxy, ethoxy or $C_1$–$C_2$-alkoxy substituted by 1 to 5 halogen atoms;
$R_8$ represents a halogen, $C_1$–$C_3$-alkyl, $C_1$–$C_3$-alkyl substituted by 1 to 7 halogen atoms, $C_1$–$C_3$-alkoxy, $C_1$–$C_3$-alkoxy substituted by 1 to 7 halogen atoms, or cyano;
U represents a grouping —CH= or —N=;
X represents —O—, —S— or —N($R_9$)—;
Y represents —O—, —S—, —S(O)—, —S(O$_2$)—, —CH$_2$—, —CO— or —N($R_9$)—, wherein
$R_9$ represents hydrogen, $C_1$–$C_4$-alkyl or alkylcarbonyl having a total of from 2 to 4 carbon atoms;
n is a number 0 or 1;
m is a number 0, 1 or 2;
p is a number 1, 2 or 3; and
Z represents one of the radicals

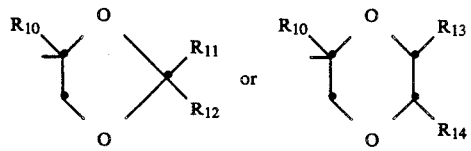

wherein
$R_{10}$ represents hydrogen, methyl or ethyl;
$R_{11}$ represents hydrogen, $C_1$–$C_6$-alkyl, $C_3$–$C_6$-cycloalkyl, $C_2$–$C_4$-alkenyl, $C_2$–$C_4$-alkynyl, alkoxyalkyl having a total of 2 to 6 carbon atoms, $C_1$–$C_6$-alkyl substituted by 1 to 7 halogen atoms, benzyl or benzyl substituted in the nucleus by a halogen atom, by a $C_1$–$C_3$-alkyl radical or by a $C_1$–$C_3$-alkoxy radical, cyanomethyl, ($C_1$–$C_2$-alkoxy)-carbonyl or the radical —CH$_2$—NH—COO—($C_1$–$C_2$-alkyl);
$R_{12}$ represents hydrogen, $C_1$–$C_6$-alkyl, phenyl, phenyl substituted by 1 to 3 substituents from the group consisting of halogen, $C_1$–$C_4$-alkyl, $C_1$–$C_3$-alkyl substituted by 1 to 7 halogen atoms, $C_2$–$C_4$-alkenyl, $C_2$–$C_4$-alkynyl, $C_{1l}$–$_{C3}$-alkoxy, $C_1$–$C_3$-alkoxy substituted by from 1 to 7 halogen atoms, alkoxyalkyl having a total of from 2 to 5 carbon atoms, $C_3$–$C_4$-alkenyloxy, $C_3$–$C_4$-alkynyloxy and $C_1$–$C_3$-alkylthio, or represents pyridyl, furan-2-yl, thien-2-yl or the radical

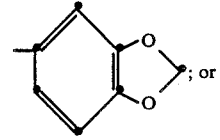

$R_{12}$ and $R_{11}$ together represent one of the groups

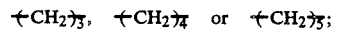

and
$R_{13}$ and $R_{14}$ each independently of the other represents hydrogen, halogen or $C_1$–$C_3$-alkyl; or
$R_{13}$ and $R_{14}$ together represent the group (Abstract continued on next page.)

$-(CH_2)_{\overline{x}}$.

Processes for the preparation of these compounds and their use in pest control, especially for controlling insects and representatives of the order Acarina, are described.

25 Claims, No Drawings

SUBSTITUTED DIOXOLAN AND DIOXAN DERIVATIVES USEFUL AS PESTICIDES

The present invention relates to novel substituted 1,3-dioxolan and 1,4-dioxan derivatives, to processes for their preparation, and to their use in pest control.

The compounds according to the invention have the formula I

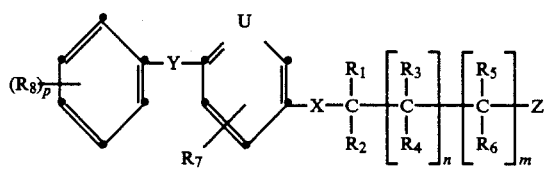

in which $R_1$, $R_2$, $R_3$, $R_4$, $R_5$ and $R_6$ each independently of the others represents hydrogen or $C_1$–$C_4$-alkyl or, if n=1, $R_2$ and $R_4$ together represent one of the radicals $-(CH_2)_3-$ or $-(CH_2)_4-$;

$R_7$ represents hydrogen, halogen, methyl, ethyl, $C_1$–$C_2$-alkyl substituted by 1 to 5 halogen atoms, methoxy, ethoxy or $C_1$–$C_2$-alkoxy substituted by 1 to 5 halogen atoms;

$R_8$ represents halogen, $C_1$–$C_3$-alkyl, $C_1$–$C_3$-alkyl substituted by 1 to 7 halogen atoms, $C_1$–$C_3$-alkoxy, $C_1$–$C_3$-alkoxy substituted by 1 to 7 halogen atoms, or cyano;

U represents a grouping —CH= or —N=;

X represents —O—, —S— or —N($R_9$)—;

Y represents —O—, —S—, —S(O)—, —S($O_2$)—, —$CH_2$—, —CO— or —N($R_9$)—, wherein $R_9$ represents hydrogen, $C_1$–$C_4$-alkyl or alkylcarbonyl having a total of from 2 to 4 carbon atoms;

n is a number 0 or 1;

m is a number 0, 1 or 2;

p is a number 1, 2 or 3; and

Z represents one of the radicals

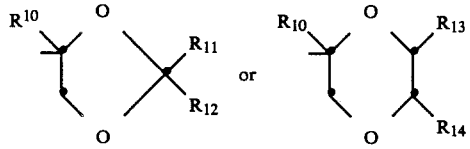

wherein $R_{10}$ represents hydrogen, methyl or ethyl;

$R_{11}$ represents hydrogen, $C_1$–$C_6$-alkyl, $C_3$–$C_6$-cycloalkyl, $C_2$–$C_4$-alkenyl, $C_2$–$C_4$-alkynyl, alkoxyalkyl having a total of 2 to 6 carbon atoms, $C_1$–$C_6$-alkyl substituted by 1 to 7 halogen atoms, benzyl or benzyl substituted in the nucleus by a halogen atom, by a $C_1$–$C_3$-alkyl radical or by a $C_1$–$C_3$-alkoxy radical, or represents cyanomethyl, ($C_1$–$C_2$-alkoxy)-carbonyl or the radical —$CH_2$—NH—COO— ($C_1$–$C_2$-alkyl);

$R_{12}$ represents hydrogen, $C_1$–$C_6$-alkyl, phenyl, phenyl substituted by 1 to 3 substituents from the group consisting of halogen, $C_1$–$C_4$-alkyl, $C_1$–$C_3$-alkyl substituted by 1 to 7 halogen atoms, $C_2$–$C_4$-alkenyl, $C_2$–$C_4$-alkynyl, $C_1$–$C_3$-alkoxy, $C_1$–$C_3$-alkoxy substituted by 1 to 7 halogen atoms, alkoxyalkyl having a total of 2 to 5 carbon atoms, $C_3$–$C_4$-alkenyloxy, $C_3$–$C_4$-alkynyloxy and $C_1$–$C_3$-alkylthio, or represents pyridyl, furan-2-yl, thien-2-yl or the radical

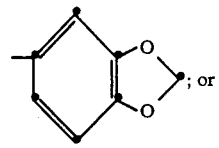

$R_{12}$ and $R_{11}$ together represent one of the groups $-(CH_2)_3-$, $-(CH_2)_4-$ or $-(CH_2)_5-$;

and $R_{13}$ and $R_{14}$ each independently of the other represents hydrogen, halogen or $C_1$–$C_3$-alkyl; or $R_{13}$ and $R_{14}$ together represent the group $-(CH_2)_4-$.

In the context of the present invention, halogen is fluorine, chlorine, bromine or iodine, preferably fluorine or chlorine.

The invention also relates to the possible isomers, including the diastereoisomers and the enantiomers, of the compounds of formula I.

The alkyl, alkoxy, haloalkyl, haloalkoxy, alkoxyalkyl, alkylthioalkyl, alkenyl and alkynyl groups may be straight-chain or branched. Examples of such groups are, inter alia, methyl, methoxy, methoxymethyl, difluoromethoxy, ethyl, ethoxy, 2-fluoroethoxy, 1,1,2,2-tetrafluoroethyl, pentafluoroethyl, 1,1,2,2-tetrafluoroethoxy, pentafluoroethoxy, propyl, isopropyl, n-butyl, n-pentyl, n-hexyl and their isomers, vinyl, 1-propen-3-yl and 1-propynyl.

Preferred cycloalkyl groups for $R_{11}$ are cyclopentyl and cyclohexyl.

According to the invention, preferred compounds of formula I are those in which $R_1$, $R_2$, $R_3$, $R_4$, $R_5$ and $R_6$ each independently of the others represents hydrogen or $C_1$–$C_4$-alkyl or, if n=1, $R_2$ and $R_4$ together represent one of the radicals $-(CH_2)_3-$ or $-(CH_2)_4-$;

$R_7$ represents hydrogen, halogen, methyl, ethyl, $C_1$–$C_2$-alkyl substituted by 1 to 5 halogen atoms, methoxy, ethoxy or $C_1$–$C_2$-alkoxy substituted by 1 to 5 halogen atoms;

$R_8$ represents halogen, $C_1$–$C_3$-alkyl, $C_1$–$C_3$-alkyl substituted by 1 to 7 halogen atoms, $C_1$–$C_3$-alkoxy, $C_1$–$C_3$-alkoxy substituted by 1 to 7 halogen atoms, or cyano;

U represents a grouping —CH= or —N=;

X represents —O—, —S— or —N($R_9$)—;

Y represents —O—, —S—, —S(O)—, —S($O_2$)—, —$CH_2$—, —CO— or —N($R_9$)—, wherein $R_9$ represents hydrogen, $C_1$–$C_4$-alkyl or alkylcarbonyl having a total of 2 to 4 carbon atoms;

n is a number 0 or 1;

m is a number 0, 1 or 2;

p is a number 1, 2 or 3; and

Z represents one of the radicals

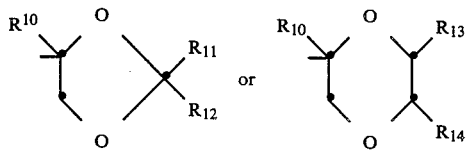

wherein $R_{10}$ represents hydrogen, methyl or ethyl;

$R_{11}$ represents hydrogen, $C_1$–$C_6$-alkyl, $C_3$–$C_6$-cycloalkyl, $C_2$–$C_4$-alkenyl, $C_2$–$C_4$-alkynyl, alkoxyalkyl having a total of 2 to 6 carbon atoms, $C_1$–$C_6$-alkyl substituted by 1 to 7 halogen atoms, benzyl, or benzyl substituted at the nucleus by a halogen atom, by a $C_1$–$C_3$-alkyl radical or by a $C_1$–$C_3$-alkoxy radical;

$R_{12}$ represents hydrogen, $C_1$–$C_6$-alkyl, phenyl, phenyl substituted by 1 to 3 substituents from the group consisting of halogen, $C_1$–$C_4$-alkyl, $C_1$–$C_3$-alkyl substituted by 1 to 7 halogen atoms, $C_2$–$C_4$-alkenyl, $C_2$–$C_4$-alkynyl, $C_1$–$C_3$-alkoxy, $C_1$–$C_3$-alkoxy substituted by 1 to 7 halogen atoms, alkoxyalkyl having a total of 2 to 5 carbon atoms, $C_3$–$C_4$-alkenyloxy, $C_3$–$C_4$-alkynyloxy and $C_1$–$C_3$-alkylthio, or represents the radical

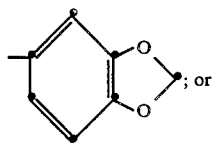

$R_{12}$ and $R_{11}$ together represent one of the radicals $(CH_2)_4$ or $(CH_2)_5$;

and $R_{13}$ and $R_{14}$ each independently of the other represents hydrogen, halogen or $C_1$–$C_3$-alkyl; or $R_{13}$ and $R_{14}$ together represent the group $(CH_2)_4$.

Attention is drawn also to compounds of formula I that are characterised in that $R_1$ and $R_3$ each independently of the other represents hydrogen, methyl or ethyl;

$R_2$, $R_4$, $R_5$ and $R_6$ represent hydrogen or, if $n=1$, $R_2$ and $R_4$ together represent one of the radicals $(CH_2)_3$ or $(CH_2)_4$;

$R_7$ represents hydrogen or halogen;

$R_8$ represents methyl, ethyl, halogen or $C_1$–$C_2$-alkyl substituted by 1 to 5 halogen atoms;

U represents a grouping —CH= or —N=;

X represents —O—, —S— or —N($R_9$)—;

Y represents —O—, —S—, —CH$_2$— or —CO—;

wherein $R_9$ represents hydrogen, methyl or acetyl;

n and m independently of each other is a number 0 or 1;

p is a number 1 or 2; and

Z represents one of the radicals

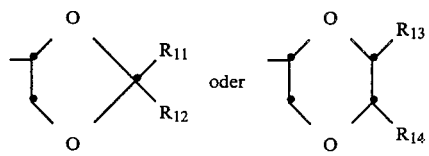

wherein $R_{11}$ represents hydrogen, $C_1$–$C_4$-alkyl, $C_3$–$C_6$-cycloalkyl, $C_2$–$C_3$-alkenyl, $C_2$–$C_3$-alkynyl, alkoxyalkyl having a total of 2 to 4 carbon atoms, $C_1$–$C_4$-alkyl substituted by 1 to 7 halogen atoms, or benzyl;

$R_{12}$ represents hydrogen, $C_1$–$C_4$-alkyl, phenyl, phenyl substituted by 1 or 2 substituents from the group consisting of halogen, $C_1$–$C_3$-alkyl, $C_1$–$C_2$-alkyl substituted by 1 to 5 halogen atoms, $C_2$–$C_4$-alkenyl, $C_2$–$C_4$-alkynyl, $C_1$–$C_3$-alkoxy, methoxy substituted by 1 to 3 halogen atoms, alkoxyalkyl having a total of 3 to 4 carbon atoms, $C_3$–$C_4$-alkenyloxy, $C_3$–$C_4$-alkynyloxy and $C_1$–$C_3$-alkylthio, or represents the radical

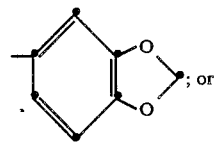

$R_{12}$ and $R_{11}$ together represent one of the radicals $(CH_2)_4$ or $(CH_2)_5$; and $R_{13}$ and $R_{14}$ each independently of the other represents hydrogen or methyl.

Also preferred are those compounds of formula I in which $R_1$ represents hydrogen or methyl;

$R_2$, $R_3$, $R_4$, $R_5$, $R_6$ and $R_7$ represent hydrogen;

$R_8$ represents fluorine, chlorine, methyl or trifluoromethyl;

U represents the grouping —CH=;

X represents —O—;

Y represents —O—;

n and m are the number 0;

p is a number 1 or 2; and

Z represents one of the radicals

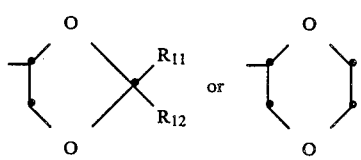

wherein $R_{11}$ represents hydrogen, $C_1$–$C_4$-alkyl, $C_3$–$C_6$-cycloalkyl, $C_2$–$C_3$-alkenyl, $C_2$–$C_3$-alkynyl, alkoxyalkyl having a total of 2 to 4 carbon atoms, or benzyl;

$R_{12}$ represents hydrogen, $C_1$–$C_4$-alkyl, $C_1$–$C_2$-alkyl substituted by from 1 to 5 halogen atoms, phenyl, phenyl substituted by 1 or 2 substituents from the group consisting of halogen and $C_1$–$C_3$-alkyl, or represents the radical

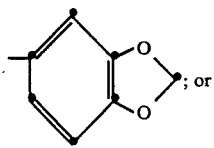;  or $R_{12}$ and $R_{11}$ together represent one of the radicals

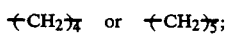

those compounds of formula I in which
$R_1$ represents hydrogen or methyl;
$R_2$, $R_3$, $R_4$, $R_5$, $R_6$ and $R_7$ represent hydrogen;
$R_8$ represents halogen or trifluoromethyl;
U represents the grouping —CH=;
X represents —O— or —S—;
Y represents —O—, —S—, —CH$_2$— or —CO—;
n and m are the number 0;
p is a number 1 or 2; and
Z represents one of the radicals

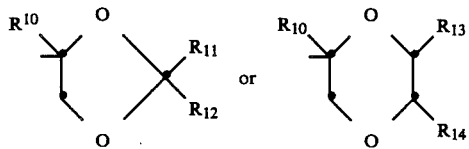

wherein
$R_{10}$ represents hydrogen or methyl;
$R_{11}$ represents hydrogen, $C_1$–$C_6$-alkyl, $C_3$–$C_6$-cycloalkyl, $C_2$–$C_4$-alkenyl, $C_2$–$C_4$-alkynyl, alkoxyalkyl having a total of 2 to 4 carbon atoms, $C_1$–$C_4$-alkyl substituted by 1 to 5 halogen atoms, benzyl, cyanomethyl, ($C_1$–$C_2$-alkoxy)-carbonyl or the radical —CH$_2$—NH—COO— ($C_1$–$C_2$-alkyl);
$R_{12}$ represents hydrogen, $C_1$–$C_6$-alkyl, phenyl substituted by 1 or 2 substituents from the group consisting of halogen, $C_1$–$C_2$-alkyl, $C_2$–$C_4$-alkenyl, $C_2$–$C_3$-alkynyl, $C_1$–$C_2$-alkoxy and $C_2$–$C_3$-alkylthio, or represents pyridyl, furan-2-yl, thien-2-yl or the radical

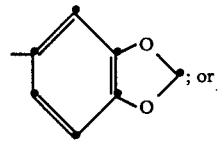;  or $R_{12}$ and $R_{11}$ together represent one of the groups

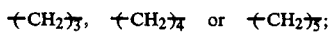

and
$R_{13}$ and $R_{14}$ each independently of the other represents hydrogen, halogen or $C_1$–$C_3$-alkyl; or
$R_{13}$ and $R_{14}$ together represent the group

;

and
those compounds of formula I in which
$R_1$, $R_2$, $R_3$, $R_4$, $R_5$, $R_6$ and $R_7$ represent hydrogen;
$R_8$ represents fluorine, chlorine or trifluoromethyl;
U represents the grouping —CH=;
X represents —O—;
Y represents —O—, —S—, —CH$_2$— or —CO—;
n and m are the number 0;
p is a number 1 or 2; and
Z represents one of the radicals

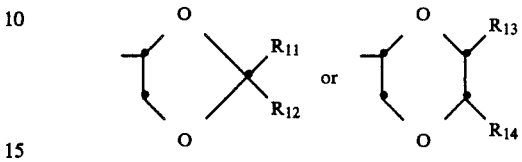

wherein
$R_{11}$ represents hydrogen, $C_1$–$C_6$-alkyl, $C_3$–$C_6$-cycloalkyl, $C_2$–$C_4$-alkenyl, $C_2$–$C_4$-alkynyl, alkoxyalkyl having a total of 2 to 4 carbon atoms, $C_1$–$C_4$-alkyl substituted by 1 to 5 fluorine or chlorine atoms, benzyl, cyanomethyl, ethoxycarbonyl or the radical —CH$_2$—NH—COO—CH$_3$;
$R_{12}$ represents hydrogen, $C_1$–$C_6$-alkyl, phenyl substituted by 1 or 2 substituents from the group consisting of fluorine, chlorine, $C_1$–$C_2$-alkyl and $C_1$–$C_2$-alkoxy, or represents pyrid-4-yl, furan-2-yl or thien-2-yl, or the radical

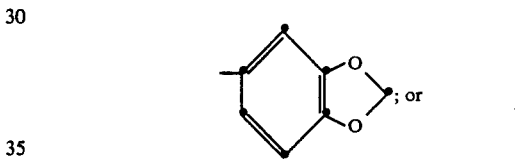;  or $R_{12}$ and $R_{11}$ together represent one of the groups

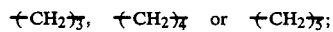

and
$R_{13}$ and $R_{14}$ each independently of the other represents hydrogen, halogen or $C_1$–$C_3$-alkyl; or
$R_{13}$ and $R_{14}$ together represent the group

.

Because of their biological activity, attention is drawn according to the invention especially to the compounds of formula Ia

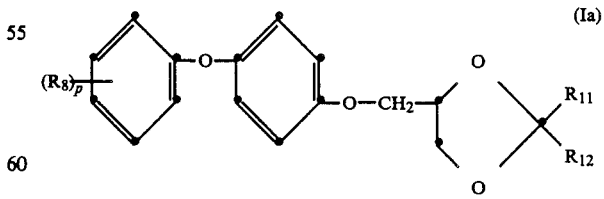

(Ia)

wherein
$R_8$ represents fluorine, chlorine or trifluoromethyl;
p is a number 1 or 2; and
$R_{11}$ and $R_{12}$ each independently of the other represents hydrogen, $C_1$–$C_4$-alkyl, $C_2$–$C_4$-methoxyalkyl, $C_1$–$C_2$-alkyl substituted by 1 to 3 halogen atoms, $C_2$–$C_3$-alkenyl or $C_2$–$C_3$-alkynyl, or $R_{11}$ and $R_{12}$ together represent one of the radicals

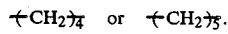

Those compounds of formula I or Ia in which p=1 and/or $R_{12}$ represents hydrogen are also of particular importance.

The compounds of formula I and Ia can be prepared in a manner known per se (see also U.S. Pat. No. 4,007,280):

(a) To that end, for example, a compound of formula II

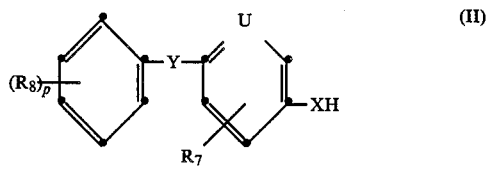

can be reacted with a compound of formula III

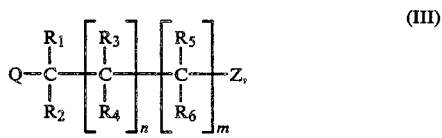

in which formulae II and III $R_1$ to $R_8$, U, X, Y, n, m, p and Z have the meanings given above and Q represents a leaving group.

(b) A compound of formula I in which Z represents the radical

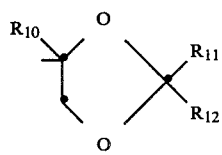

can be obtained by condensing a compound of formula IV

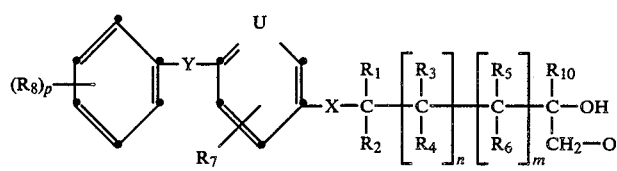

in the presence of an acidic catalyst with a compound of formula V or Va

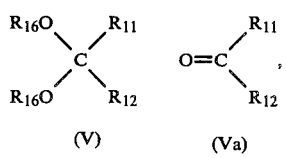

in which formulae IV, V and Va $R_1$ to $R_{10}$, U, X, Y, n, m, p, $R_{11}$ and $R_{12}$ have the meanings given above and $R_{16}$ represents $C_1$–$C_4$-alkyl, preferably methyl or ethyl.

Process (a) is preferably carried out in the presence of a solvent or diluent that is inert towards the reactants and in the presence of at least one equivalent of an acid acceptor or of a basic substance respectively. Suitable acid acceptors and bases are especially tertiary amines, such as trialkylamines and pyridine, and also hydrides, hydroxides, oxides, carbonates and hydrogen carbonates of alkali metals and alkaline earth metals, and also alkali metal alcoholates, such as, for example, potassium t-butoxide and sodium methoxide etc. Depending on the nature of the solvents used, the reaction temperature is usually in the range of from −5° C. to +140° C., preferably from 0° to 60° C. In the starting compound of formula III, Q represents a usual leaving group, such as, for example, a halogen atom, the mesyloxy group or the tosyloxy group.

Process (b) is generally carried out in the presence of an inert solvent or diluent and an acidic catalyst. As acidic catalysts there are used, for example, sulphonic acids, such as methanesulphonic or p-toluenesulphonic acid, including the acidic ion exchanger resins containing sulpho groups, Lewis acids, such as boron trifluoridediethyl ether or boron trifluoride-dimethyl ether complexes, and also mineral acids, such as sulphuric acid or phosphoric acid.

Depending on the nature of the solvents used, the reaction temperature is in the range of approximately from 30° to 150° C., preferably from 60° to 120° C.

The above-described processes are carried out usually under normal or elevated pressure and preferably in an inert solvent or diluent. Suitable solvents and diluents for process (a) are, for example, ethers and ethereal compounds, such as diethyl ether, diisopropyl ether, dioxan, 1,2-dimethoxyethane and tetrahydrofuran; amides, such as N,N-dialkylated carboxylic acid amides; sulpholane and dimethyl sulphoxide. Suitable solvents and diluents for process (b) are, for example, aliphatic, aromatic and halogenated hydrocarbons, especially benzene, toluene, xylenes, chloroform, dichloromethane, chlorobenzene, hexane and cyclohexane.

The starting materials of formulae II to Va are known or, if novel, they can be prepared by methods analogous to known ones and then constitute also an object of the present invention.

For example, the diols of formula IV can be obtained (see U.S. Pat. Nos. 4,590,282 and 4,097,581) by reacting a compound of formula II with a hydroxymethylalkylene oxide of formula VII

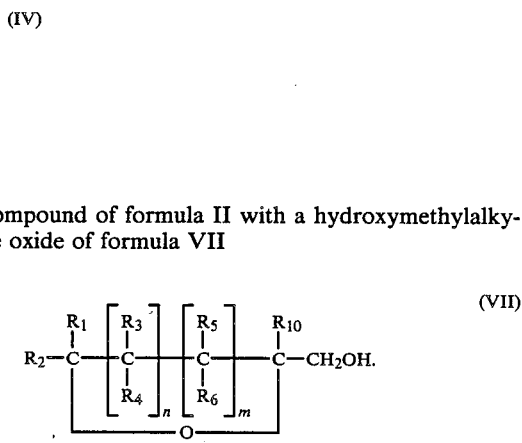

The compounds of formulae I and Ia may be in the form of mixtures of different enantiomeric forms, or they may be formed in synthesis. The mixtures of diastereoisomers or the racemates of formulae I and Ia can be resolved into the individual forms by known methods. A compound of formula I is therefore to be understood as comprising all the individual diastereoisomeric or enantiomeric forms and the mixtures thereof.

Certain 4-(4-phenoxy)-phenoxymethyl-1,3-dioxolans are already known as insecticides from U.S. Pat. No. 4,097,581. 1,3-dioxolan and 1,4-benzodioxin derivatives of similar structure and their use as pesticides are subject matter of U.S. Pat. No. 4,590,282. The compounds of formula I according to the invention differ from those known compounds essentially by the presence of a phenyl group mandatorily substituted by 1 to 3 $R_8$ radicals.

Surprisingly, it has been found that the compounds of formula I of the invention are excellently suitable for controlling a variety of pests of animals and plants as well as soil pests. The compounds of formula I can thus be used for controlling insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera and mites and ticks of the order Acarina.

The compounds of formulae I and Ia are suitable for controlling plant-destructive insects in ornamentals and crops of useful plants, in particular in cotton crops (e.g. *Spodoptera littoralis* and *Heliothis virescens*). The compounds of formula I are also effective against soil insects (e.g. *Aulacophora femoralis, Chortophila brassicae, Diabrotica balteata, Pachnodal savignyi* and *Scotia ypsilon*), and especially against sucking insects, such as aphids (e.g. *Myzus persicae, Aphis craccivora* and *Aonidiella aurantii,* and also other representatives of the family Coccidae). The compounds of this invention are also active as ovicides in plant protection, especially for controlling plant-destructive insects, e.g. *Cydia pomonella, Lobesia botrana* and *Adoxophyes reticulana*.

The compounds of formula I are also very effective against flies, e.g. *Musca domestica*, and mosquito larvae, further against stock pests, e.g. *Sitophilus orizae* and *Rhizopertha dominica*.

The compounds of formulae I and Ia of the invention are particularly effective against plant-destructive acarids (spider mites e.g. of the families Tetranychidae, Tarsonemidae, Eriophydae, Tyroglyphidae and Glycyphagidae) and also against ectoparasitic acarids (mites and ticks e.g. of the families Ixodidae, Argasidae, Sarcoptidae and Dermanyssidae) that attack productive livestock. A number of the compounds of this invention have good acaricidal-ovicidal activity and leaf penetration properties. The compounds of the invention are particularly suitable for controlling the following species of mites which attack crops of fruit and vegetables: *Tetranychus urticae, Tetranychus cinnabarinus, Panonychus ulmi, Bryobia rubrioculus, Panonychus citri, Eriophyes piri, Eriophyes ribis, Eriophyes vitis, Tarsonemus pallidus, Phyllocoptes vitis* and *Phyllocoptruta oleiVora*.

The acaricidal or insecticidal activity can be substantially broadened and adapted to prevailing circumstances by addition of other insecticides and/or acaricides. Examples of suitable additives include: organophosphorus compounds, nitrophenols and derivatives thereof, formamidines, ureas, pyrethroids and also carbamates and chlorinated hydrocarbons.

The good pesticidal activity of the compounds of formulae I and Ia of the invention corresponds to a mortality of at least 50–60% of the above pests.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing at least one compound (active ingredient) of formula I and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ethyl acetate, propyl myristate or propyl palmitate, ketones such as cyclohexanone, strongly polar solvents such as N-methyl-2-pyrrolidone, dimethyl sulphoxide or dimethylformamide, as well as vegetable oils or epoxidised vegetable oils such as epoxidised coconut oil or soybean oil; silicone oils or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactant" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Further suitable surfactants are also the fatty acid methyltaurin salts.

More frequently, however, so-called synthetic surfactants are used, especially fatty sulphonates, fatty sulphates, sulphonated benzimidazole derivatives or alkylarylsulphonates.

The fatty sulphonates or sulphates are usually in the form of alkali metal salts, alkaline earth metal salts or unsubstituted or substituted ammonium salts and contain a $C_8$–$C_{22}$-alkyl radical which also includes the alkyl moiety of acyl radicals, e.g. the sodium or calcium salt of lignosulphonic acid, of dodecylsulphate, or of a mixture of fatty alcohol sulphates obtained from natural fatty acids. These compounds also comprise the salts of sulphated and sulphonated fatty alcohol/ethylene oxide adducts. The sulphonated benzimidazole derivatives preferably contain 2 sulphonic acid groups and one fatty acid radical containing 8 to 22 carbon atoms. Examples of alkylarylsulphonates are the sodium, calcium or triethanolamine salts of dodecylbenzenesulphonic acid, dibutylnaphthalenesulphonic acid, or of a condensate of naphthalenesulphonic acid and formaldehyde.

Also suitable are corresponding phosphates, e.g. the salts of the phosphoric acid ester of an adduct of p-nonylphenol with 4 to 14 moles of ethylene oxide, and phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$-alkyl radical and, as further substituents, unsubstituted or halogenated lower alkyl, benzyl or hydroxy-lower alkyl radicals. The salts are preferably in the form of halides, methylsulphates or ethylsulphates, e.g. stearyltrimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I, 1 to 99.9% of a solid or liquid adjuvant, and 0 to 25%, especially 0.1 to 25%, of a surfactant, percentages relating to weight.

Whereas commercial compositions are preferably formulated as concentrates, the end user will normally employ dilute formulations or preparations containing e.g. 0.1 to 1000 ppm of the active compound.

The compositions may also contain further additives, such as stabilisers, anti-foams, viscosity regulators, binders, tackifiers and fertilisers or other active ingredients for achieving special effects.

EXAMPLE 1

(a) Preparation of 1,2-dihydroxy-3-[4-(4-fluorophenoxy)]-phenoxypropane (starting material)

0.7 g of tetramethylammonium chloride is added to a solution of 71.4 g of 4-fluorophenoxyphenol in 70 ml of xylene, the whole is heated to 60° C., and then 29.6 g of glycerol glycide are added dropwise, within a period of approximately 30 minutes, while stirring. The reaction mixture is then further stirred for approximately 16 hours at 90° C. For working up, 200 ml of n-hexane are slowly added to the reaction mixture at approximately 60° C., the whole is cooled to 20° C. while stirring, and the precipitate which has formed is filtered off. The crude product so obtained is recrystallised from isopropanol and n-hexane. In this manner, the title compound of formula

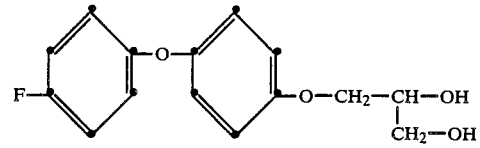

is obtained in the form of colourless crystals with a melting point of 86°–87° C.

The following compounds of formula IV are prepared in analogous manner, if appropriate with purification by chromatography (eluant: methylene chloride/diethyl ether 1:1):

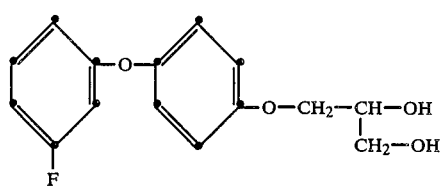

m.p. 76–78° C.

-continued
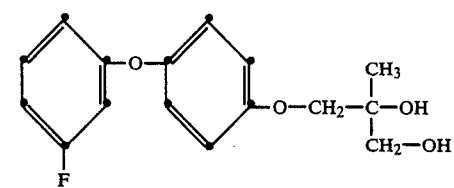
m.p. 63-64° C.
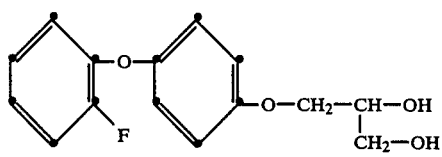
m.p. 52-54° C.
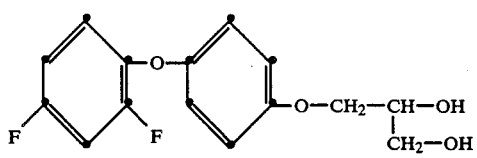
m.p. 64-65° C.
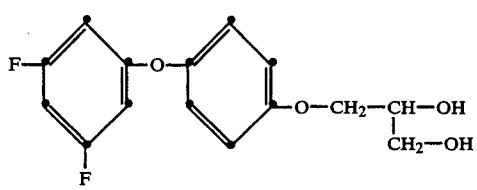
m.p. 74-75° C.
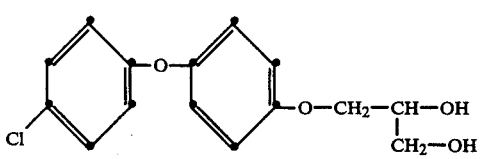
m.p. 109-110° C.
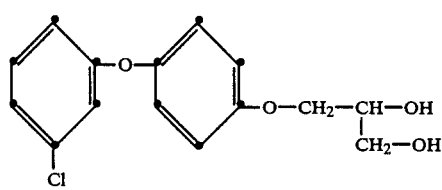
m.p. 60-62° C.
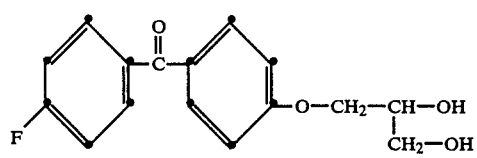
m.p. 94-96° C.
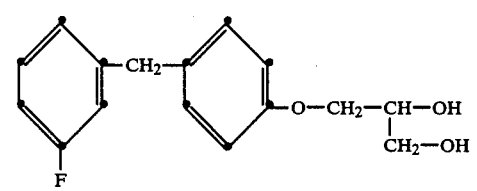
m.p. 81-82° C.
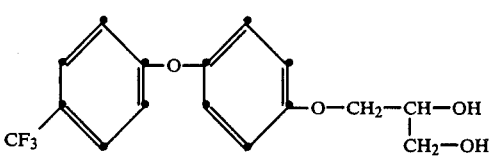
m.p. 87-88° C.

(b) Preparation of 4-[4-(4-fluorophenoxy)]-phenoxymethyl-2-ethyl-1,3-dioxolan 8 g of propionaldehyde diethyl acetal are added dropwise, within a period of 10 minutes, while stirring at reflux temperature, to a solution of 13.9 g of the 1,2-dihydroxy-3-[4-(4-fluroophenoxy)]phenoxypropane prepared in accordance with (a) and 40 mg of p-toluenesulphonic acid in 75 ml of cyclohexane. After stirring for one hour at that temperature, the ethanol which has formed is distilled off continuously over a short Vigreux column within a period of approximately 2½ hours. The reaction mixture is then washed with 10% sodium carbonate solution and then with water, the cyclohexane solution is dried over sodium sulphate, the cyclohexane is distilled off under a water-jet vacuum, and the residue is chromatographed on silica gel (eluant: n-hexane/diethyl ether 19:1). The title compound (compound no. 1) of formula

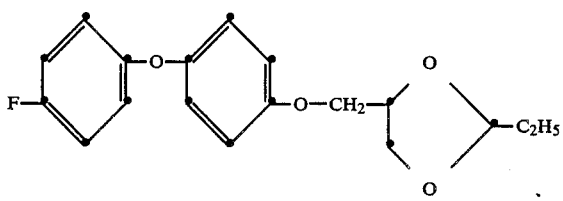

obtained in this manner has a melting point of 47°–48° C. (mixture of diastereoisomers).

EXAMPLE 2

Preparation of 4-[4-(4-fluorophenoxy)]-phenoxymethyl-2-isopropyl-1,3-dioxolan

A solution of 13.9 g of 1,2-dihydroxy-3-[4-(4-fluorophenoxy)]-phenoxypropane, 5.1 g of isobutyraldehyde and 50 mg of p-toluenesulphonic acid in 150 ml of benzene is heated for 5 hours while stirring in a water separator. The reaction mixture is then washed repeatedly first with 10% sodium carbonate solution and then with water, and is then dried over sodium sulphate and filtered. The benzene is distilled off from the resulting filtrate in vacuo. The crude product is chromatographed on silica gel (eluant: ether/n-hexane 1:20), the pure title compound having a melting point of 62°–64° C. (compound no. 2) of formula

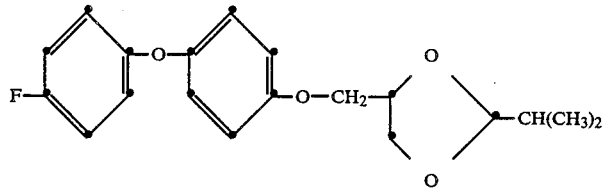

being obtained in the form of a mixture of diastereoisomers.

EXAMPLE 3

Preparation of 4-[4-(4-fluorophenoxy)]-phenoxymethyl-2,2-dimethyl-1,3-dioxolan:

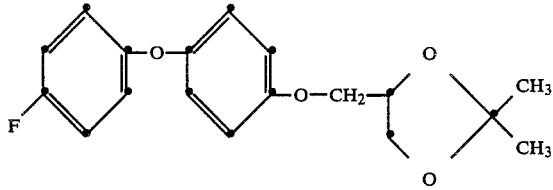

(a) 6.4 g of 4-(4-fluorophenoxy)-phenol are reacted with 3.5 g of potassium tert.-butoxide in anhydrous dimethyl sulphoxide, a solution of the potassium salt of that phenol being obtained. A solution of 9.1 g of R-(−)-2,2-dimethyl-1,3-dioxolan-4-methanoltoluene-4-sulphonate in 20 ml of dimethyl sulphoxide is added dropwise to the solution obtained above in a nitrogen atmosphere at 10° C., while stirring, and the whole is then stirred for a further 20 hours at 20°–22° C.

For working up, the reaction mixture is poured into 300 ml of ice-water and extracted four times with 100 ml of diethyl ether. The combined ether phases are washed repeatedly with water and dried over sodium sulphate. After the ether has been distilled off, the residue is purified further by chromatography on 250 g of silica gel (eluant: diethyl ether/hexane 1:20), pure (S)-4-[4-(4-fluorophenoxy)]-phenoxymethyl-2,2-dimethyl-1,3-dioxolan being obtained: $n_D^{20}=1.5345$, $[\alpha]_D^{20}$: +5.2±0.3 (CHCl$_3$) (compound no. 3).

(b) In analogous manner there is obtained from the potassium salt of 4-(4-fluorophenoxy)-phenol and S-(+)-2,2-dimethyl-1,3-dioxolan-4-methanol-toluene-4-sulphonate in dimethyl sulphoxide the enantiomeric (R)-4-[4-(4-fluorophenoxy)]-phenoxymethyl-2,2-dimethyl-1,3-dioxolan: $n_D^{20}=1.5350$, $[\alpha]_D^{20}$: −5.0±0.3 (CHCl$_3$) (compound no. 3a).

The optical purity of the two enantiomers characterised under (a) and (b) above was checked by MPLC chromatography (medium pressure liquid chromatography) on cellulose triacetate. It is ~99.8% for the S compound and ~99.4% for the R compound.

EXAMPLE 4

(a) Preparation of 2-methanesulphonylmethyl-6-methyl-1,4-dioxan (starting material)

13.7 ml of methanesulphonic acid chloride are added dropwise, over a period of approximately 30 minutes, while stirring at 0° to 5° C., to a solution of 21.1 g of 2-hydroxymethyl-6-methyl-1,4-dioxan, 15.2 g of pyridine and 0.6 g of 4-dimethylaminopyridine in 80 ml of dichloromethane. After stirring for a further 18 hours at room temperature, the reaction mixture is extracted repeatedly with 1N hydrochloric acid and then washed with water until neutral. After the organic phase, which has been separated off, has been dried over sodium sulphate and the solvent has been distilled off completely, the title compound of formula

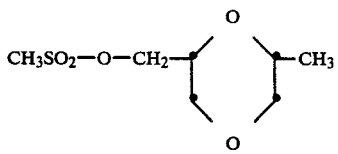

is obtained. The $^1$H-proton resonance spectrum corresponds to this structure; $n_D^{22} = 1.4607$.

(b) Preparation of
2-[4-(3-fluorophenoxy)]-phenoxymethyl-6-methyl-1,4-dioxan

A freshly prepared solution of 3.6 g of potassium tert.-butoxide in 20 ml of dimethyl sulphoxide is added while cooling with ice to a solution of 6.2 g of 4-(3-fluorophenoxy)-phenol in 20 ml of dimethyl sulphoxide. To the resulting solution of the potassium salt of that phenol there is then added dropwise at 10° C., over a period of approximately 30 minutes, a solution of 8 g of the 2-methanesulphonylmethyl-6-methyl-1,4-dioxan prepared as above in accordance with (a), in 20 ml of dimethyl sulphoxide. The reaction mixture is then stirred for a further 16 hours at 22° C. The mixture is then poured onto ice-water and extracted repeatedly with diethyl ether/hexane (1:1). The combined organic phases are washed with 10% potassium hydroxide solution and then with water until neutral, and dried over sodium sulphate. The solvents are then distilled off. The title compound of formula

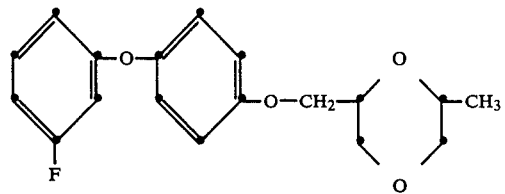

which has a refractive index $n_D^{22} = 1.5445$ (compound no. 4) is obtained by chromatography on silica gel (eluant: hexane/ethyl acetate 6:1). The elementary analysis and the 1H-NMR spectrum correspond to the above structure.

The following compounds according to the invention of formula:

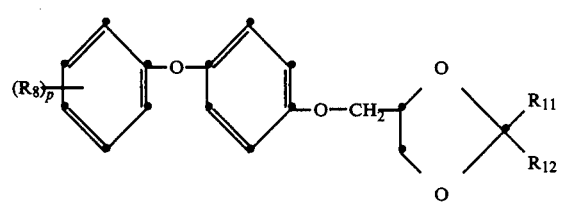

are also prepared analogously to the procedures described above, all the compounds—except where indicated—being in the form of mixtures of their diastereoisomers:

| Comp. No. | R$_8$ | p | R$_{11}$ | R$_{12}$ | Physical data |
|---|---|---|---|---|---|
| 5 | 4-F | 1 | —CH=CH$_2$ | H | $n_D^{21} = 1.5477$ |
| 6 | 4-F | 1 | —C≡CH | H | m.p. 74–76° C. |
| 7 | 4-F | 1 | —CH$_3$ | —CH$_3$ | m.p. 84–86° C.* |
| 8 | 3-F | 1 | —CH=CH$_2$ | H | $n_D^{20} = 1.5493$ |
| 9 | 3-F | 1 | —CH$_3$ | —CH$_3$ | m.p. 60–62° C.* |
| 10 | 3-F | 1 | —C$_2$H$_5$ | H | $n_D^{20} = 1.5379$ |
| 11 | 2-F | 1 | —C$_2$H$_{hd 5}$ | H | $n_D^{20} = 1.5361$ |
| 12 | 4-F | 1 | —(CH$_2$)$_2$—CH$_3$ | H | $n_D^{20} = 1.5301$ |
| 13 | 3-F | 1 | —(CH$_2$)$_2$—CH$_3$ | H | $n_D^{20} = 1.5321$ |
| 14 | 4-F | 1 | —CH$_2$—CH(CH$_3$)$_2$ | H | $n_D^{20} = 1.5257$ |
| 15 | 3-F | 1 | —CH(CH$_3$)$_2$ | H | m.p. approx. 32° C. |
| 16 | 2-F | 1 | —(CH$_2$)$_2$—CH$_3$ | H | $n_D^{20} = 1.5318$ |
| 17 | 2-F | 1 | —CH(CH$_3$)$_2$ | H | $n_D^{20} = 1.5321$ |
| 18 | 4-F | 1 | —(CH$_2$)$_5$— | | m.p. 53–55° C.* |
| 19 | 3-F | 1 | —CH=CH—CH$_3$ | H | $n_D^{20} = 1.5443$ |
| 20 | 4-F | 1 | —CH$_2$—CH—CH$_3$<br>            |<br>           OCH$_3$ | H | $n_D^{20} = 1.5281$ |
| 21 | 4-F | 1 | —C$_2$H$_5$ | —CH$_3$ | m.p. 57–59° C. |
| 22 | 2-F | 1 | —CH$_3$ | H | $n_D^{20} = 1.5410$ |
| 23 | 2-F | 1 | —CH$_3$ | H | $n_D^{23} = 1.5410$ |
| 24 | 3-F | 1 | —CH$_2$=CH—CH$_3$ | H | $n_D^{20} = 1.5443$ |
| 25 | 3-F | 1 | —CH$_2$CH(OCH$_3$)—CH$_3$ | H | $n_D^{20} = 1.5300$ |
| 26 | 4-F | 1 | —CH$_3$ | H | diastereoisomer A: m.p. 46–47° C. |
| 26a | 4-F | 1 | —CH$_3$ | H | diastereoisomer B: $n_D^{21} = 1.5428$ |
| 27 | 4-F | 1 | —CH(CH$_3$)—C$_2$H$_5$ | H | $n_D^{19} = 1.5369$ |
| 28 | 2-F, 4-F | 2 | —C$_2$H$_5$ | H | $n_D^{20} = 1.5280$ |
| 29 | 2-F, 4-F | 2 | —CH(CH$_3$)$_2$ | H | $n_D^{20} = 1.5225$ |
| 30 | 4-F | 1 |  | H | m.p. 89–91° C. |

-continued

| Comp. No. | $R_8$ | p | $R_{11}$ | $R_{12}$ | Physical data |
|---|---|---|---|---|---|
| 31 | 3-F | 1 | 4-Cl-phenyl | H | m.p. 59–61° C. |
| 32 | 4-F | 1 | 4-Cl-phenyl | H | $n_D^{23} = 1.5782$ |
| 33 | 4-F | 1 | 3,4-Cl$_2$-phenyl | H | $n_D^{20} = 1.5861$ |
| 34 | 3-F | 1 | 3,4-Cl$_2$-phenyl | H | $n_D^{21} = 1.5849$ |
| 35 | 4-F | 1 | phenyl | —CH$_3$ | $n_D^{20} = 1.5359$ |
| 36 | 4-F | 1 | —(CH$_2$)$_5$— | | m.p. 53–55° C.° |
| 37 | 4-F | 1 | 4-F-phenyl | H | m.p. 73–74° C. |
| 38 | 4-F | 1 | —C(CH$_3$)$_3$ | H | $n_D^{22} = 1.5379$ |
| 39 | 4-F | 1 | —(CH$_2$)$_3$— | | m.p. 72–73° C.* |
| 40 | 3-F | 1 | —CH$_2$Cl | H | $n_D^{20} = 1.5504$ |
| 41 | 3-F | 1 | —(CH$_2$)$_3$ | | $n_D^{21} = 1.5414*$ |
| 42 | 4-F | 1 | —CH$_2$Br | H | $n_D^{20} = 1.5769$ |
| 43 | 4-F | 1 | —CO—OC$_2$H$_5$ | H | $n_D^{20} = 1.5419$ |
| 44 | 4-Cl | 1 | —C$_2$H$_5$ | H | $n_D^{20} = 1.5529$ |
| 45 | 4-Cl | 1 | —C$_3$H$_7$(n) | H | m.p. 41–43° C. |
| 46 | 4-F | 1 | —CHCl$_2$ | H | $n_D^{20} = 1.5669$ |
| 47 | 3-F, 5-F | 2 | —CH=CH$_2$ | H | m.p. 46–48° C. |
| 48 | 3-F, 5-F | 2 | —C$_2$H$_5$ | H | m.p. 32–34° C. |
| 49 | 3-F, 5-F | 2 | —C$_3$H$_7$(n) | H | $n_D^{20} = 1.5262$ |
| 50 | 3-F | 1 | —C(CH$_3$)$_3$ | H | $n_D^{20} = 1.5270$ |
| 51 | 4-F | 1 | —C(CH$_3$)$_3$ | H | $n_D^{20} = 1.5289$ |
| 52 | 3-F | 1 | —CH$_2$—O—CH$_3$ | H | $n_D^{20} = 1.5390$ |
| 53 | 3-F | 1 | pyridyl | H | $n_D^{20} = 1.5733$ |
| 54 | 4-F | 1 | pyridyl | H | m.p. 60–63° C. |
| 55 | 3-F | 1 | —NH—CO—OCH$_3$ | H | m.p. 65–66° C. |
| 56 | 3-F | 1 | —CH=C(CH$_3$)$_2$ | H | m.p. 67–69° C. |
| 57 | 3-F | 1 | —C≡CH | H | $n_D^{20} = 1.5539$ |
| 58 | 3-F | 1 | —(CH$_2$)$_5$—CH$_3$ | H | $n_D^{20} = 1.5245$ |
| 59 | 3-F | 1 | —(CH$_2$)$_4$—CH$_3$ | H | $n_D^{20} = 1.5260$ |

-continued

| Comp. No. | $R_8$ | p | $R_{11}$ | $R_{12}$ | Physical data |
|---|---|---|---|---|---|
| 60 | 3-F | 1 | —$C_4H_9$(n) | H | $n_D^{22}$ = 1.5290 |
| 61 | 3-F | 1 | cyclopropyl | —$CH_3$ | diastereoisomer A (as racemate): m.p. 69–70° C. |
| 61a | 3-F | 1 | cyclopropyl | —$CH_3$ | diastereoisomer B (as racemate): m.p. 44–46° C. |
| 62 | 3-F | 1 | —CH=$CH_2$ | —$CH_3$ | diastereoisomer A (as racemate): $n_D^{22}$ = 1.5370 |
| 62a | 3-F | 1 | —CH=$CH_2$ | —$CH_3$ | diastereoiosmer B (as racemate): $n_D^{22}$ = 1.5350 |
| 63 | 3-Cl | 1 | —$C_2H_5$ | H | $n_D^{20}$ = 1.5560 |
| 64 | 3-F | 1 | —$CH_2$—C≡N | H | m.p. 85–87° C. |
| 65 | 3-F, 5-F | 2 | —CH($CH_3$)$_2$ | H | $n_D^{20}$ = 1.5221 |
| 66 | 2-F, 4-F | 2 | —CH=$CH_2$ | H | $n_D^{22}$ = 1.5376 |
| 67 | 3-Cl | 1 | —$C_3H_7$(n) | H | $n_D^{22}$ = 1.5481 |
| 68 | 3-Cl | 1 | —CH=$CH_2$ | H | $n_D^{22}$ = 1.5639 |
| 69 | 2-F | 1 | pyridyl | H | diastereoisomer A: $n_D^{20}$ = 1,5862 |
| 69a | | | | | diastereoisomer B: $n_D^{20}$ = 1.5822 |
| 70 | 4-$CF_3$ | 1 | —$C_2H_5$ | H | m.p. 62–63° C. |
| 71 | 3-F | 1 | —$CCl_2$—$CF_3$ | H | $n_D^{20}$ = 1.5695 |
| 72 | 3-F | 1 | —$CH_2$—$CH_2Cl$ | H | $n_D^{20}$ = 1.5341 |
| 73 | 3-F | 1 | —($CH_2$)— | | m.p. 94–95° C.* |
| 74 | 3-F | 1 | —$CH_2$—CH—CH— with $CH_2$—CH—$CH_2$ bridge | | m.p. 36–38° C. |
| 75 | 4-F | 1 | cyclohexyl (H) | H | $n_D^{22}$ = 1.5350 |
| 76 | 2-F | 1 | —$CH_2Cl$ | H | $n_D^{21}$ = 1.5618 |
| 77 | 4-F | 1 | —($CH_2$)$_4$— | | m.p. 88–90° C.* |
| 78 | 4-F | 1 | —$CH_2Cl$ | H | $n_D^{22}$ = 1.5381 |
| 79 | 4-F | 1 | phenyl-$C_2H_5$ | H | m.p. 84–85° C. |
| 80 | 4-F | 1 | benzodioxole | H | m.p. 83–85° C. |
| 81 | 3-F | 1 | benzodioxole | H | m.p. 47–50° C. |

-continued

| Comp. No. | $R_8$ | p | $R_{11}$ | $R_{12}$ | Physical data |
|---|---|---|---|---|---|
| 82 | 4-F | 1 | H | H | m.p. 34–36° C. |
| 83 | 3-F | 1 | —CH$_3$ | H | $n_D^{20}$ = 1.5420 |
| 84 | 3-F | 1 | —C(CH$_3$)=CH$_2$ | H | m.p. 48–50° C. |
| 85 | 3-F | 1 | —(CH$_2$)$_4$— | | m.p. 94–95° C.* |
| 86 | 3-F | 1 | (furan-2-yl) | H | $n_D^{22}$ = 1.5620 |
| 87 | 3-F | 1 | (thiophen-2-yl) | H | m.p. 51–53° C. |
| 88 | 3-F | 1 | —C$_2$H$_5$ | H | m.p. 84–86° C. |
| 89 | 3-F | 1 | —CH$_2$—(phenyl) | H | m.p. ~30° C. |

*not a diastereoisomeric mixture but a racemate

The following compounds of formula I are also prepared analogously to the procedures described above:

| Compound No. | Structure | Physical data |
|---|---|---|
| 90 | F-phenyl-O-phenyl-O-CH$_2$-(1,3-dioxolane) | m.p. 57–58° C. |
| 91 | (2-F-phenyl)-O-phenyl-O-CH$_2$-(1,3-dioxolane) | m.p. 60–62° C. |
| 92 | (3-F-phenyl)-O-phenyl-O-CH$_2$-(1,3-dioxolane) | m.p. 65–67° C. |
| 93 | (4-F-phenyl)-C(=O)-phenyl-O-CH$_2$-(1,3-dioxolan-2-yl)-CH(CH$_3$)$_2$ | m.p. 112–114° C. |

-continued

| Compound No. | Structure | Physical data |
|---|---|---|
| 94 | F-C6H4-C(=O)-C6H4-O-CH2-C(-O-)(-O-)-C2H5 (dioxolane) | m.p. 55–57° C. |
| 95 | F-C6H4-C(=O)-C6H4-O-CH2-C(-O-)(-O-)-C3H7(n) (dioxolane) | m.p. 54–57° C. |
| 96 | F-C6H4-S-C6H4-O-CH2-C(-O-)(-O-)-C2H5 (dioxolane) | $n_D^{20} = 1{,}5479$ |
| 97 | F-C6H4-S-C6H4-O-CH2-C(CH3)(-O-)(-O-)-C2H5 (dioxolane) | $n_D^{20} = 1{,}5309$ |
| 98 | F-C6H4-CH2-C6H4-O-CH2-(1,3-dioxane) | m.p. 66–67° C. |
| 99 | F-C6H4-CH2-C6H4-O-CH2-C(-O-)(-O-)-C3H7(n) (dioxolane) | m.p. 56–57° C. |
| 100 | F-C6H4-O-C6H4-O-CH2-C(-O-)(-O-)-CH3 (dioxolane) | m.p. ~35° C. |

The following compounds of formula I can be prepared in a manner analogous to that described above:

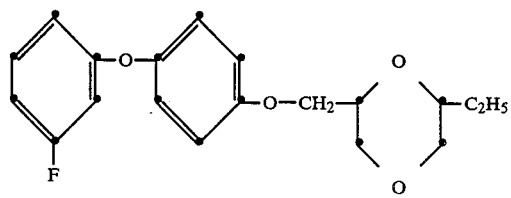

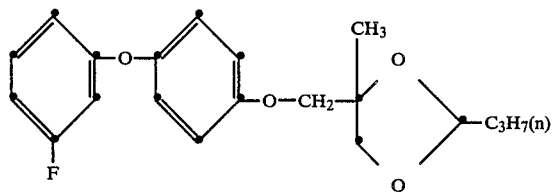

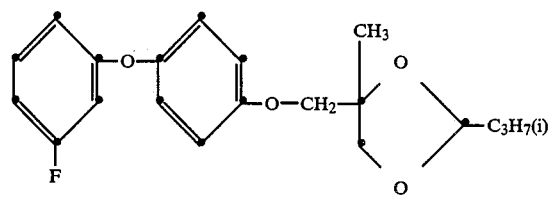

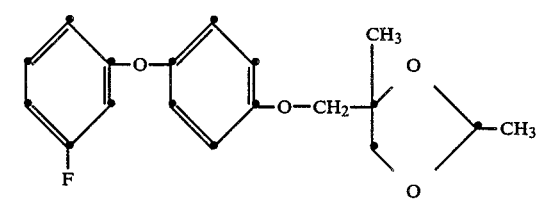

EXAMPLE 5

Formulation Examples for liquid active ingredients of formula I according to Examples 1 to 4 (throughout, percentages are by weight)

| 1. Emulsifiable concentrates | (a) | (b) | (c) |
|---|---|---|---|
| compound according to the Preparatory Examples | 25% | 40% | 50% |
| calcium dodecylbenzenesulphonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2. Solutions | (a) | (b) | (c) | (d) |
|---|---|---|---|---|
| compound according to the Preparatory Examples | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| ligroin (boiling range 160–190° C.) | — | — | 94% | — |

These solutions are suitable for application in the form of microdrops.

| 3. Granulates | (a) | (b) |
|---|---|---|
| compound according to the Preparatory Examples | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
|---|---|---|
| compound according to the Preparatory Examples | 2% | 5% |
| highly dispersed silicic acid | 1% | 5% |
| talcum | 97% | — |
| kaolin | — | 90% |

Ready for use dusts are obtained by intimately mixing the carriers with the active ingredient.

Formulation Examples for solid active ingredients of formula I according to Examples 1 to 4 (throughout, percentages are by weight)

| 5. Wettable powders | (a) | (b) | (c) |
|---|---|---|---|
| compound according to the Preparatory Examples | 20% | 50% | 75% |
| sodium lignosulphonate | 5% | 5% | — |
| sodium laurylsulphate | 3% | — | 5% |
| sodium diisobutylnaphthalene-sulphonate | — | 6% | 10% |
| octylphenol polyethylene glycol ether (7–8 moles of ethylene oxide) | — | 2% | — |
| highly dispersed silicic acid | 5% | 10% | 10% |
| kaolin | 67% | 27% | — |

The active ingredient is mixed with the adjuvants and the mixture is thoroughly ground in a suitable mill, affording wettable powders which can be diluted with water to give suspensions of the desired concentration.

| 6. Emulsifiable concentrates | (a) | (b) |
|---|---|---|
| compound according to the Preparatory Examples | 10% | 10% |
| octylphenol polyethylene glycol ether (4–5 moles of ethylene oxide) | 3% | — |
| calcium dodecylbenzenesulphonate | 3% | — |
| castor oil polyglycol ether (36 moles of ethylene oxide) | 4% | — |
| castor oil thioxilate | — | 25% |
| cyclohexanone | 30% | — |
| butanol | — | 15% |
| xylene mixture | 50% | — |
| ethyl acetate | — | 50% |

Emulsions of any required concentration can be obtained from this concentrate by dilution with water.

| 7. Dusts | (a) | (b) |
|---|---|---|
| compound according to the Preparatory Examples | 5% | 8% |
| talcum | 95% | — |
| kaolin | — | 92% |

Ready for use dusts are obtained by mixing the active ingredient with the carrier and grinding the mixture in a suitable mill.

| 8. Extruder granulate | |
|---|---|
| compound according to the Preparatory Examples | 10% |
| sodium lignosulphonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 9. Coated granulate | |
|---|---|
| compound according to the Preparatory Examples | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 10. Suspension concentrate | |
|---|---|
| compound according to the Preparatory Examples | 40% |
| ethylene glycol | 10% |
| nonylphenol polyethylene glycol ether (15 moles of ethylene oxide) | 6% |
| sodium lignosulphonate | 10% |
| carboxymethylcellulose | 1% |
| 37% aqueous formaldehyde solution | 0.2% |
| silicone oil in the form of a | 75% |
| aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 6

Action against *Lucilia sericata*

1 ml of an aqueous solution containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

In this test, compounds of the formula I according to Examples 1 to 4 show good activity against *Lucilia sericata*.

EXAMPLE 7

Action against *Aedes aegypti*

A concentration of 100 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker containing the test compound. Mortality counts are made after 2 and 7 days.

In this test, compounds of formula I according to Examples 1 to 4 show good activity against *Aedes aegypti*.

EXAMPLE 8

Action against *Aonidiella aurantii*

(a) Immersion test—potato tubers

Small potato tubers are infested with crawlers of *Aonidiella aurantii* (California red scale) by keeping the potatoes for about 24 hours in direct contact with large pumpkins which are heavily infested with Aonidiella, so that ultimately a population of 200 to 300 crawlers is present on each potato. When the crawler population on the potatoes has attained the 2nd nymphal stage, i.e. after about 14 days, the potatoes are immersed, using pincers, for about 2 to 3 minutes in an aqueous emulsion formulation which contains the respective test compound in a concentration of 50 ppm. The treated potatoes are dried and then kept for 10 to 12 weeks in plastic containers which are ringed at the top with glue to trap the winged males. Evaluation is subsequently made by comparing the state of the treated Aonidiella population with that of untreated control populations. This is done by counting the number of males and assessing the development of females (formation of scales) and the production of crawlers of the first generation of progeny.

(b) Spray treatment—citrus plants

Citrus trifoliata cuttings are brought into close contact with a pumpkin which is heavily infested with Aonidiella (q.v. test (a) above), so that each cutting is populated with about 150 to 200 crawlers which have migrated from the pumpkin. When the crawler population has attained the 2nd nymphal stage, i.e. after about 14 days, the infested cuttings are sprayed to drip point with an aqueous emulsion formulation containing the respective test compound in a concentration of 50 ppm. After about 10 to 12 weeks, an evaluation is made of the development of the population (percentage of male and female scales) and of the production of crawlers compared with untreated controls.

Compounds 1–20, 25, 27–35, 37–41 75, 77–83 and 90–92 of formula I according to Examples 1 to 4 were 100% effective in this test.

EXAMPLE 9

Insecticidal stomach poison action

Cotton plants about 25 cm high, in pots, are sprayed with an aqueous emulsion containing the respective test compound in a concentration of 400 ppm.

After the spray coating has dried, the treated cotton plants are put into metal pots (3 plants per pot) and populated with 50 Spodoptera larvae in the $L_1$ stage. Each pot is then covered with a glass plate. The test is carried out at 28° C. and about 60% relative humidity. The percentage mortality of the test insects compared with untreated controls is determined after 96 hours.

Compounds of formula I according to Examples 1 to 4 exhibit good activity in this test.

EXAMPLE 10

Action against ticks

Adult females of the cattle tick, *Boophilus microplus*, which are replete with blood are used as test organisms. The test is carried out with 10 ticks each of an OP-resistant strain (e.g. Biarra strain) and of a normal sensitive strain (e.g. Yeerongpilly strain). The ticks are affixed in the dorsal position to plates to which double-sided adhesive tape has been applied and then contacted for 1 hour with a cotton wool swab which is impregnated with a solution or aqueous emulsion containing the test compound in a concentration of 400 ppm. After removal of the cotton wool swab, the ticks are dried overnight at 24° C. and then kept in a controlled environment chamber under constant conditions (28° C., 80% relative humidity) for 4 weeks until oviposition has taken place and the larvae have started to hatch. Evaluation is made by making a mortality count and determining the percentage inhibition of fertile egg deposits (inhibition of embryogenesis and hatching) compared with untreated controls.

Compounds 1–11, 13–21, 25, 27, 28, 39, 77, 78, 83, 90 and 100 of formula I according to Examples 1 to 4 were 100% effective in this test.

EXAMPLE 11

Action against ticks: killing action in various development stages

About 50 larvae, about 25 nymphs or about 10 imagines of each of the tick species *Rhipicephalus bursa*, *Amblyomma hebraeum* and *Boophilus microplus* are used as test organisms. The test organisms are immersed for a short time in aqueous emulsions containing the respective test compound in a concentration of 800 ppm. The emulsions, which are contained in test tubes, are then absorbed by cotton wool, and the wetted test organisms are left in the test tubes which have thus been contaminated. Evaluation of the percentage mortality is made 3 days later in the case of the larvae and 14 days later in the case of the nymphs and imagines.

Compounds of formula I according to Examples 1 to 4 exhibit good activity in this test.

EXAMPLE 12

Ovicidal action against *Cydia pomonella, Adoxophyes reticulana* and *Lobesia botrana*

Egg deposits not more than 24 hours old of the above fruit pests are immersed three times for a few seconds in an aqueous acetone solution of the respective test compound having a concentration of 400 ppm. After the test solution has dried, the eggs are placed in petri dishes (diameter: 5 cm) and kept at a temperature of 26° C. and 55% relativae humidity. The treated egg deposits of *Cydia pomonella* (codling moth) are placed between two round paper filters in the petri dish. The egg deposits of *Adoxophyes reticulana* (summer fruit tortrix moth) and *Lobesia botrana* (vine moth) are placed between two round cloth filters beneath the cover of the petri dish, into the bottom part of which a normal Lepidopter feed has been poured. Evaluation is made 6 days later by determining the percentage of larvae which have hatched from the treated eggs, using untreated controls for comparison purposes.

Compounds of formula I of Examples 1 to 4 exhibit good activity in this test.

EXAMPLE 13

Chemosterilisation action against *Nilaparvata lugens*

The test is carried out with growing plants. To this end, 4 rice plants (thickness of stem ca. 5 cm, height ca. 20 cm) are planted in pots (diameter: 8 cm).

The plants are sprayed on a rotary table with 5 ml of an aqueous emulsion formulation containing the test compound used in a concentration of 400 ppm. After the spray coating has dried, each plant is populated with 4 adult females and 2 males. To revent the insects from escaping, a transparent plastic cylinder is slipped over each infested pot and sealed with a gauze cover. The insects remain for 6 days on the treated plants for oviposition. The surviving insects are counted and then removed.

The rice plants with the egg deposits are incubated for 14 days at 20° C. and 60% relative humidity. A count is made of the young cicadas which have hatched out during this time. The percentage reduction of progeny (chemosterilisation effect) is determined by comparing the number of larvae which have hatched out on the treated plants with that of the larvae which have hatched out on untreated control plants.

Compounds of formula I according to Examples 1 to 4 exhibit good activity in this test.

EXAMPLE 14

Action against *Bemisia tabaci*

(a) Aplication of the test compound before infestation

Cotton plants in the cotyledon stage, in pots, are sprayed to drip point with an aqueous emulsion formulation of the respective test compound in a concentration of 400 ppm. After the spray coating has dried, 40 adults of *Bemisia tabaci* (white fly) are kept on each plant in plastic cylinders. A first evaluation is made by determining the percentage mortality of the adults present on the plants 3 days after infestatioan. The surviving adults are removed. A second evaluation is made 24 hours after infestatioan by determining the percentage mortality of the nymphs, pupae and adults of the first generatioan of progeny. The test is carried out in a controlled environment chamber at 25° C. and a relative humidity of ca. 50–60%.

(b) Application of the test compound after infestation

Cotton plants (untreated) in the cotyledon stage, in pots, are populated as described in (a) with *Bemisia tabaci* (white fly) such that 40 unsexed adults are present on each plant. After oviposition over 3 days, all adults are removed. Ten days after infestation, i.e. at a time when about two-thirds of the nymphs are in the 1st nymphal stage and one third are in the 2nd nymphal stage, the infested plants are sprayed to drip point with an aqueous emulsion-formulation of the test compound (concentration: 400 ppm). A count of dead and living nymphs, pupae and adults is made 24 days after infestation. The test is carried out in a controlled environment chamber at 25° C. and at a relative humidity of about 50–60%.

Compounds of formula I of Examples 1 to 4 show good effectiveness in this test.

EXAMPLE 15

Action against storage pests—*Sitophilus orizae* and *Rhizopertha dominica*

100 g of wheat grains are thoroughly mixed in a 100 ml plastic beaker with 1 ml of an aqueous emulsion formulation of the respective test compound, said aqueous emulsion formulation containing the test compound in a concentration such that, based on the weight of the wheat grains, the final concentration is 100 ppm. Then 25 unsexed adults of *Sitophilus orizae* (rice weevil) and *Rhizopertha dominica* (lesser grain borer) are put into each beaker (filled with 100 g of treated wheat grains). After infestation, the beakers are kept in the dark at 26°-28° C. and 60-65% relative humidity. The percentage mortality of the adults is determined one week after infestation and the percentage reduction of the first progeny is determined 8 weeks after infestation.

The compounds of formula I according to Examples 1 to 4 were very effective in this test.

I claim:

1. A compound of formula I

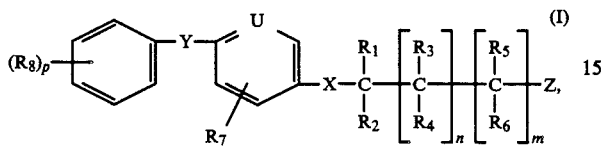

in which $R_1$, $R_2$, $R_3$, $R_4$, $R_5$ and $R_6$ each independently of the others represents hydrogen or $C_1$-$C_4$-alkyl or, if $n=1$, $R_2$ and $R_4$ together represent one of the radicals —$(CH_2)_3$— or —$(CH_2)_4$—;

$R_7$ represents hydrogen, halogen, methyl, ethyl, $C_1$-$C_2$-alkyl-substituted by 1 to 5 halogen atoms, methoxy, ethoxy or $C_1$-$C_2$-alkoxy substituted by 1 to 5 halogen atoms;

$R_8$ represents halogen, $C_1$-$C_3$-alkyl substituted by 1 to 7 halogen atoms, $C_1$-$C_3$-alkoxy, $C_1$-$C_3$-alkoxy substituted by 1 to 7 halogen atoms, or cyano;

U represents a grouping —CH═;
X represents —O— or —S—;
Y represents —O— or —S—, wherein
n is the number 0 or 1;
m is the number 0;
p is the number 1, 2 or 3; and
Z represents

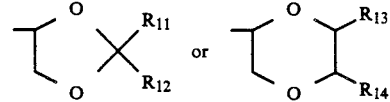

wherein $R_{10}$ represents hydrogen or methyl;

$R_{11}$ represents hydrogen, $C_1$-$C_6$-alkyl, $C_3$-$C_6$-cycloalkyl, $C_2$-$C_4$-alkenyl, $C_2$-$C_4$-alkynyl, alkoxyalkyl having a total of 2 to 6 carbon atoms, $C_1$-$C_6$-alkyl substituted by 1 to 7 halogen atoms, benzyl or benzyl substituted in the nucleus by a halogen atom, by a $C_1$-$C_3$-alkyl radical or by a $C_1$-$C_3$-alkoxy radical, or represents cyanomethyl, ($C_1$-$C_2$-alkoxy)-carbonyl or the radical —$CH_2$—NH—COO—($C_1$-$C_2$-alkyl);

$R_{12}$ represents hydrogen, $C_1$-$C_6$-alkyl, phenyl, phenyl substituted by 1 to 3 substituents from the group consisting of halogen, $C_1$-$C_4$-alkyl, $C_1$-$C_3$-alkyl substituted by 1 to 7 halogen atoms, $C_2$-$C_4$-alkenyl, $C_2$-$C_4$-alkynyl, $C_1$-$C_3$-alkoxy, $C_1$-$C_3$-alkoxy substituted by 1 to 7 halogen atoms, alkoxyalkyl having a total of 2 to 5 carbon atoms, $C_3$-$C_4$-alkenyloxy, $C_3$-$C_4$-alkynyloxy and $C_1$-$C_3$alkylthio, or represents pyridyl or the radical

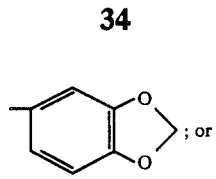

$R_{12}$ and $R_{11}$ together represent one of the groups —$(CH_2)_3$—, —$(CH_2)_4$— or —$(CH_2)_5$—; and $R_{13}$ and $R_{14}$ each independently of the other represents hydrogen or $C_1$-$C_3$-alkyl.

2. A compound of formula I according to claim 1, characterised in that $R_1$ and $R_3$ each independently of the other represents hydrogen, methyl or ethyl;

$R_2$, $R_4$, $R_5$ and $R_6$ represent hydrogen or, if $n=1$, $R_2$ and $R_4$ together represent one of the radicals

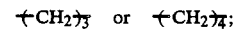

$R_7$ represents hydrogen or halogen;

$R_8$ represents halogen or $C_1$-$C_2$-alkyl substituted by 1 to 5 halogen atoms;

U represents a grouping —CH═;
X represents —O— or —S—;
Y represents —O— or —S—, wherein
n is the number 0 or 1;
m is the number 0;
p is the number 1 or 2; and
Z represents

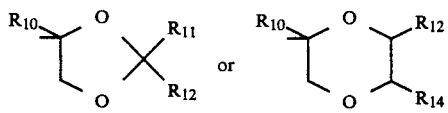

wherein $R_{11}$ represents hydrogen, $C_1$-$C_4$-alkyl, $C_3$-$C_6$-cycloalkyl, $C_2$-$C_3$-alkenyl, $C_2$-$C_3$-alkynyl, alkoxyalkyl having a total of 2 to 4 carbon atoms, $C_1$-$C_4$-alkyl substituted by 1 to 7 halogen atoms, or benzyl; $R_{12}$ represents hydrogen, $C_1$-$C_4$-alkyl, phenyl, phenyl substituted by 1 or 2 substituents from the group consisting of halogen, $C_1$-$C_3$-alkyl, $C_1$-$C_2$-alkyl substituted by 1 to 5 halogen atoms, $C_2$-$C_4$alkenyl, $C_2$-$C_4$-alkynyl, $C_1$-$C_3$-alkoxy, methoxy substituted by 1 to 3 halogen atoms, alkoxyalkyl having a total of 3 to 4 carbon atoms, $C_3$-$C_4$-alkenyloxy, $C_3$-$C_4$-alkynyloxy and $C_1$-$C_3$-alkylthio, or represents the radical

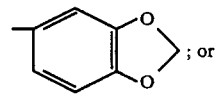

$R_{12}$ and $R_{11}$ together represent one of the radicals

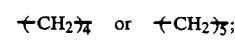

and $R_{13}$ and $R_{14}$ each independently of the other represents hydrogen or methyl.

3. A compound of formula I according to claim 2, characterised in that $R_1$ represents hydrogen or methyl;

R$_2$, R$_3$, R$_4$, R$_5$, R$_6$ and R$_7$ represent hydrogen;
R$_8$ represents fluorine, chlorine, or trifluoromethyl;
U represents the grouping —CH=;
X represents —O—;
Y represents —O—;
n and m are the number 0;
p is a number 1 or 2; and
Z represents one of the radicals

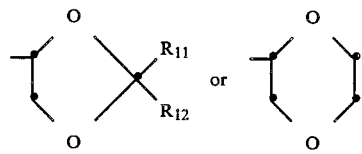

wherein
R$_{11}$ represents hydrogen, C$_1$–C$_4$-alkyl, C$_3$–C$_6$-cycloalkyl, C$_2$–C$_3$-alkenyl, C$_2$–C$_3$-alkynyl, alkoxyalkyl having a total of 2 to 4 carbon atoms, or benzyl;
R$_{12}$ represents hydrogen, C$_1$–C$_4$-alkyl, phenyl, phenyl substituted by 1 or 2 substituents from the group consisting of halogen and C$_1$–C$_3$-alkyl, or represents the radical

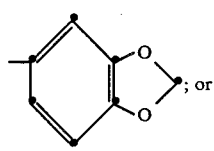

R$_{12}$ and R$_{11}$ together represent one of the radicals

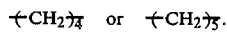

4. A compound according to claim 2 of formula Ia

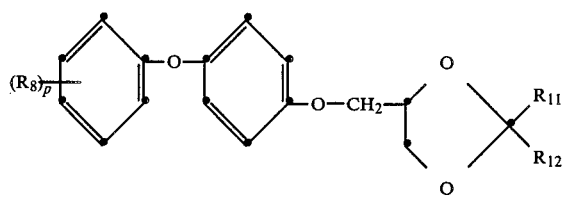

wherein
R$_8$ represents fluorine, chlorine or trifluoromethyl;
p is a number 1 or 2; and
R$_{11}$ represents hydrogen, C$_1$–C$_4$-alkyl, C$_2$–C$_4$-methoxyalkyl, C$_1$–C$_2$-alkyl substituted by 1 to 3 halogen atoms, C$_2$–C$_3$-alkenyl or C$_2$–C$_3$-alkynyl,
R$_{12}$ represents hydrogen or C$_1$–C$_4$-alkyl or R$_{11}$ and R$_{12}$ together represent one of the radicals

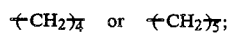

5. A compound according to claim 1, characterised in that p=1.

6. A compound according to claim 1, characterised in that R$_{12}$ represents hydrogen.

7. A compound according to claim 6 of formula

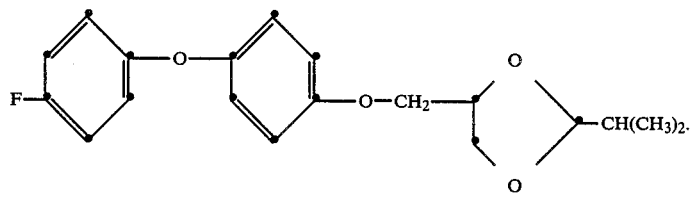

8. A compound according to claim 5 of formula

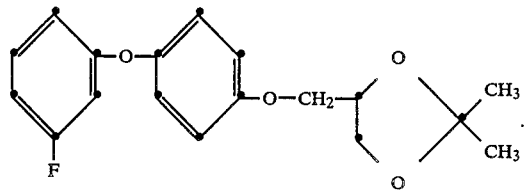

9. A compound according to claim 6 of formula

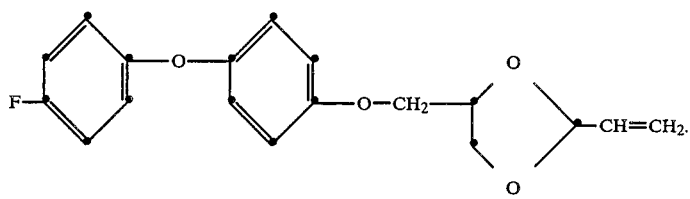

10. A compound according to claim 6 of formula

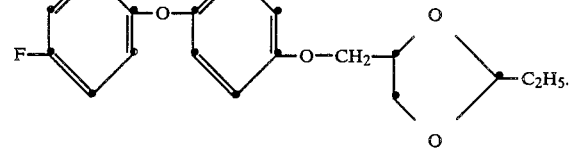

11. A compound according to claim 6 of formula

12. A compound according to claim 6 of formula
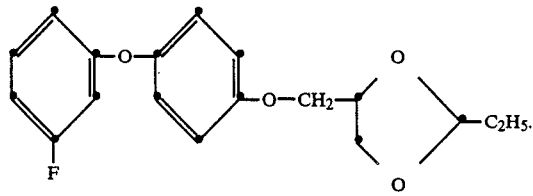
14. A compound according to claim 5 of formula
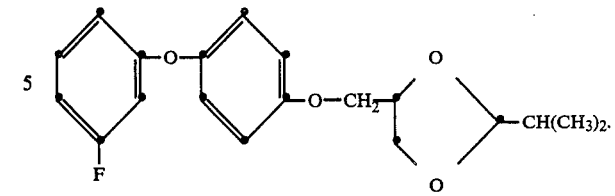
15. A compound according to claim 6 of formula
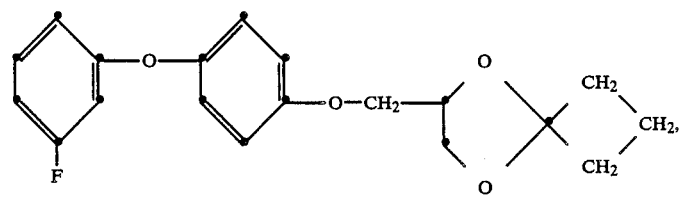
16. A compound according to claim 4 of formula
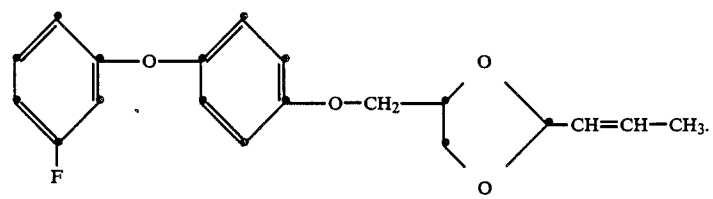
17. A compound according to claim 6 of formula
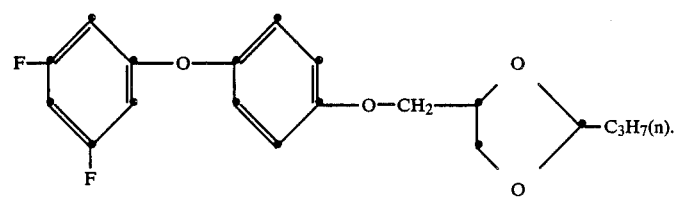
13. A compound according to claim 6 of formula
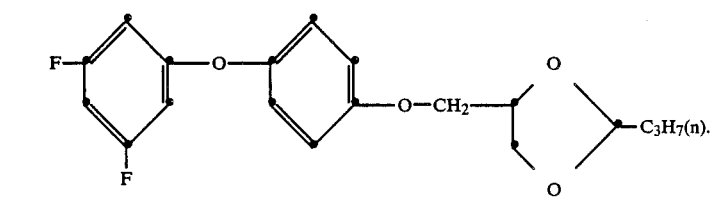
18. A compound according to claim 4 of formula
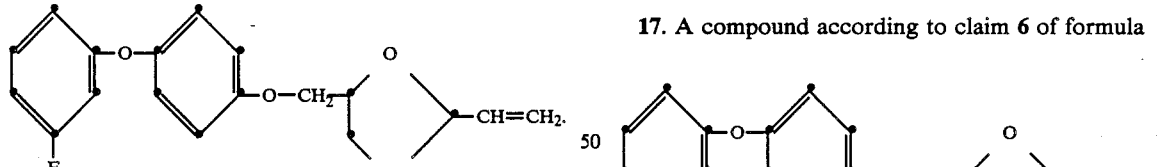
19. A compound according to claim 1 of formula
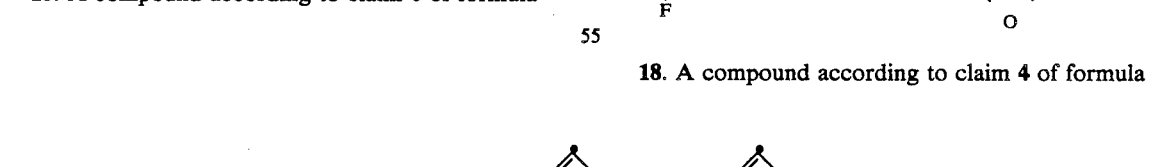

20. A compound according to claim 6 of formula

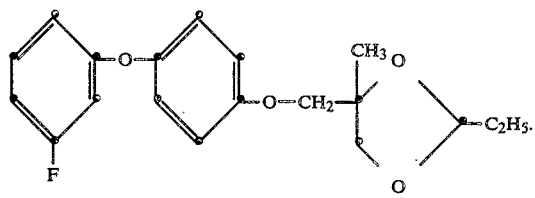

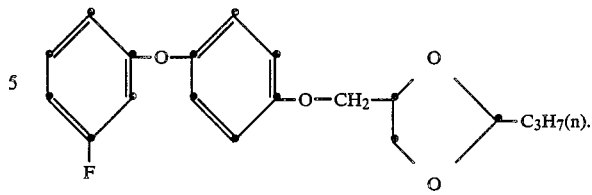

21. A method for controlling pests selected from insects and representatives of the order Acarina, characterised in that said pests, or the various stages of development thereof, or their habitat, is/are brought into contact or treated with a pesticidally effective amount of a compound of formula I according to claim 1 or with a composition containing a pesticidally effective amount of that compound together with adjuvants and carriers.

22. A method according to claim 21 for controlling plant-destructive sucking insects.

23. A method according to claim 22 for controlling insects of the family Coccidae.

24. A method according to claim 21 for controlling larval stages of plant-destructive insects.

25. A pesticidal composition which comprises as active ingredient an effective amount of a compound according to claim 1 together with a pesticidally acceptable carrier or other adjuvant.

* * * * *